(12) United States Patent
Holmes

(10) Patent No.: US 6,874,249 B2
(45) Date of Patent: Apr. 5, 2005

(54) CONTINUOUS PATH VARIABLE WIDTH LIGHT ATTENUATION DEVICE FOR ELECTROMAGNETIC ENERGY SPOT CURE SYSTEM

(75) Inventor: Mark Holmes, Waterford, CT (US)

(73) Assignee: Henkel Corporation, Rocky Hill, CT (US)

( * ) Notice: Subject to any disclaimer, the term of this patent is extended or adjusted under 35 U.S.C. 154(b) by 0 days.

(21) Appl. No.: 10/473,206

(22) PCT Filed: Aug. 9, 2002

(86) PCT No.: PCT/US02/25359
§ 371 (c)(1),
(2), (4) Date: Sep. 29, 2003

(87) PCT Pub. No.: WO03/014677
PCT Pub. Date: Feb. 20, 2003

(65) Prior Publication Data
US 2004/0111913 A1 Jun. 17, 2004

Related U.S. Application Data
(60) Provisional application No. 60/311,062, filed on Aug. 9, 2001.

(51) Int. Cl.$^7$ ................................................. F26B 3/34
(52) U.S. Cl. ........................... 34/275; 34/277; 34/245; 34/255; 34/259; 34/266; 34/308
(58) Field of Search ........................ 34/277, 275, 245, 34/248, 255, 259, 266, 268, 307, 308; 250/504 R, 504 H; 362/250, 286

(56) References Cited

U.S. PATENT DOCUMENTS

| | | | |
|---|---|---|---|
| 3,733,709 A | 5/1973 | Bassemir et al. ................. 34/4 |
| 3,967,385 A | 7/1976 | Culbertson ....................... 34/4 |
| 4,020,356 A | 4/1977 | Brahme ....................... 250/510 |
| 4,025,795 A | 5/1977 | Lackore et al. ............. 250/504 |
| 4,644,899 A | 2/1987 | Glaus .......................... 118/642 |
| 4,707,773 A | 11/1987 | Miyamoto ................... 362/303 |
| 5,444,814 A | 8/1995 | Hofius, Sr. .................. 392/407 |
| 5,722,761 A | 3/1998 | Knight ......................... 362/96 |

Primary Examiner—Kenneth Rinehart
(74) Attorney, Agent, or Firm—Steven C. Bauman

(57) ABSTRACT

An electromagnetic energy spot curing system is provided which utilizes a template which moves relative to a source of radiation in the electromagnetic spectrum, such as an ultraviolet (UV) lamp. A channel is formed through the template of varying widths so that during the course of relative movement, different intensities of radiation emanating from the source is continuously passed through the channel and applied to a desired location, typically a curable material.

32 Claims, 5 Drawing Sheets

CONTINUOUS PATH VARIABLE WIDTH LIGHT ATTENUATION DEVICE FOR ELECTROMAGNETIC ENERGY SPOT CURE SYSTEM

CROSS-REFERENCE TO RELATED APPLICATION

This application claims priority to Provisional Application, Ser. No. 60/311,062, filed on Aug. 9, 2001 and entitled "Continuous Path, Variable Width Light Attenuation Device For Electromagnetic Energy Spot Cure System".

FIELD OF THE INVENTION

The present invention relates to a curing system utilizing radiation in the electromagnetic spectrum (e.g., ultraviolet; infrared), such as a UV spot curing system, and, more particularly, relates to a UV curing lamp assembly including a template having a channel formed therethrough for varying the amount of UV energy applied to a desired location.

BACKGROUND OF RELATED TECHNOLOGY

UV spot curing lamps are well known in the prior art for curing various curable materials and compounds, such as adhesives. UV spot curing systems are used in various applications including the curing of industrial sealants for potting electronics, bonding plastics in the medical industry and the curing of dental filling materials, amongst other applications. At times, it is desired to control the amount of UV energy that is irradiated upon a substance. For example, a photo-polymerizable adhesive may require varying degrees of UV energy intensity to achieve desired final polymer properties including adhesion to a substrate and shrinkage.

It has been known to place a rotating template in alignment with a UV lamp to vary UV energy intensity, where the template is formed with a plurality of discrete holes, each hole having a different dimension. In this manner, the intensity of the applied UV energy is controlled, both by the size of the holes as well as the spacing in-between. As is readily appreciated, the template portions between the holes will shield a material from the UV energy, thereby, resulting in discontinuous UV energy applications. It has, however, been found that further enhanced control over the intensity of UV energy application is desired.

SUMMARY OF THE INVENTION

The subject invention provides a template having a continuous channel formed therethrough. The template is aligned with an electromagnetic energy source, such as a UV lamp, so that electromagnetic energy passes through at least a portion of the channel. Upon relative movement between the electromagnetic energy source and the template, varying intensities of electromagnetic energy are allowed to continuously pass therethrough during course of the relative movement.

In a desired embodiment, a channel is formed of varying widths, having a generally arcuate form which extends between first and second rounded ends of different diameters. The channel includes sides which extend between and blend with the ends. In addition, a driver, e.g., a step motor, is provided to rotate the template relative to the electromagnetic energy source to cause relative motion therebetween. The channel includes a central axis which is defined about a single radius extending from the axis of rotation of the template. It is further desired that the length of the channel be selected so that the movement of the channel across the electromagnetic energy source is synchronized with the opening and closing of a shutter.

These and other features of the invention will be better understood through a study of the following detailed description and accompanying drawings.

DETAILED DESCRIPTION OF THE INVENTION

The subject invention relates to an electromagnetic energy spot curing system which utilizes a source of radiation found in the electromagnetic spectrum (e.g., ultraviolet (UV); infrared). To describe the invention and illustrate its functioning, reference is made herein to the use of a UV lamp. It is to be understood that the UV lamp can be interchanged with other sources of electromagnetic energy. In addition, the electromagnetic energy source may provide electromagnetic energy of varying intensities and/or of varying wavelengths (e.g., various types of radiation).

Figure 1:
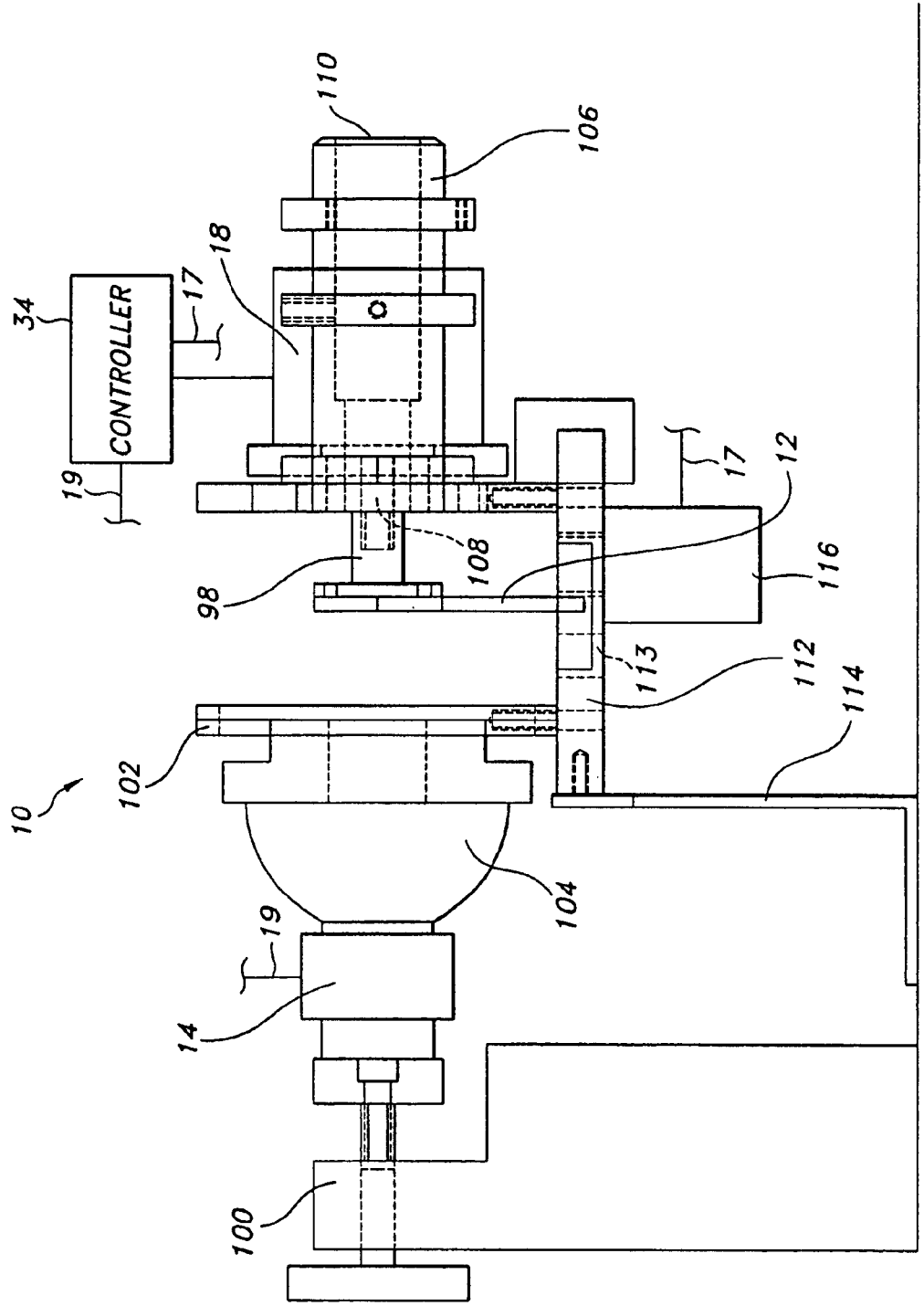
FIGS. 1 and 2 are side and top views, respectively, of an electromagnetic energy spot curing system in accordance with the subject invention.
Figure 2:
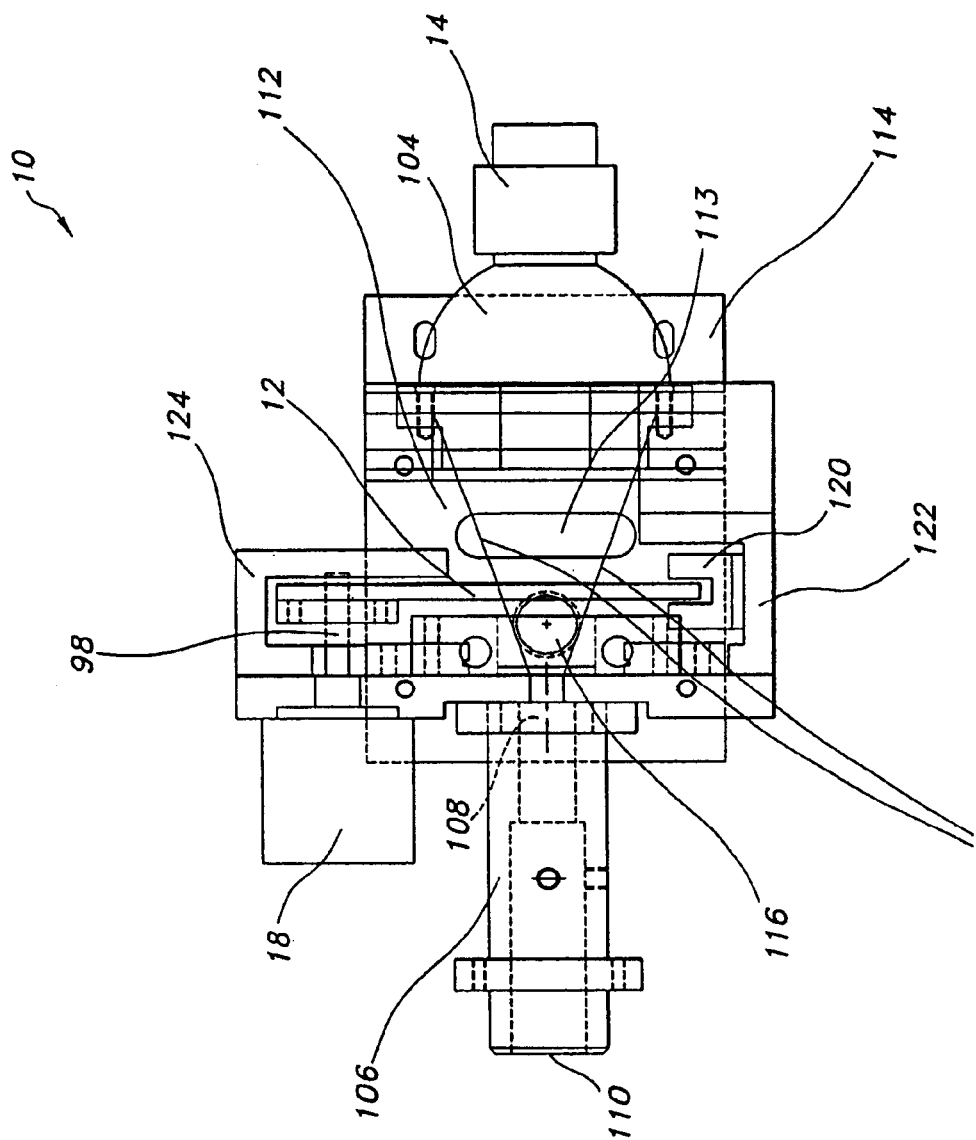

With reference to FIGS. 1 and 2, an electromagnetic energy spot curing system is generally shown and designated therein with the reference numeral 10.

The system 10 includes a template 12, and a UV lamp 14. The system 10 is configured to regulate UV energy emanating therefrom in irradiating a curable material. As described below, relative motion is generated between the template 12 and the UV lamp 14. Desirably, the template 12 is rotated by a motor 18 being coupled thereto using any technique known to those skilled in the art, including a simple shaft connection (e.g., connection through motor shaft 98). Any driver known to those skilled in the art may be interchanged with the motor 18.

The UV lamp 14 is mounted between a lamp retainer 100 and a lamp mounting plate 102. The UV lamp 14 preferably is connected to an elliptic reflector 104 so that the energy emanated from the UV lamp 14 is focused. A light guide 106 is positioned opposite the template 12 from the UV lamp 14 with a focused UV energy beam E being directed into an inlet aperture 108 of the light guide 106 (see FIG. 2). The light guide 106 may be of any type known in the prior art, and is preferably of the liquid-filled type. The light guide 106 acts to at least partially collimate the UV beam E, and the beam is emitted from the light guide 106 via end 110. As is readily apparent, the end 110 is directed to the location to be irradiated.

To ensure alignment of the UV lamp 14, the template 12 and the light guide 106, it is preferred that all three components be fixed to a common base plate 112 to minimize misalignment therebetween. A rear support bracket 114 may be fastened to the base plate 112 to rigidify the structure. In addition, a cooling channel 113 may be formed through the base plate 112 which allows air flow to pass therethrough to cool the lamp 14.

Figure 3:
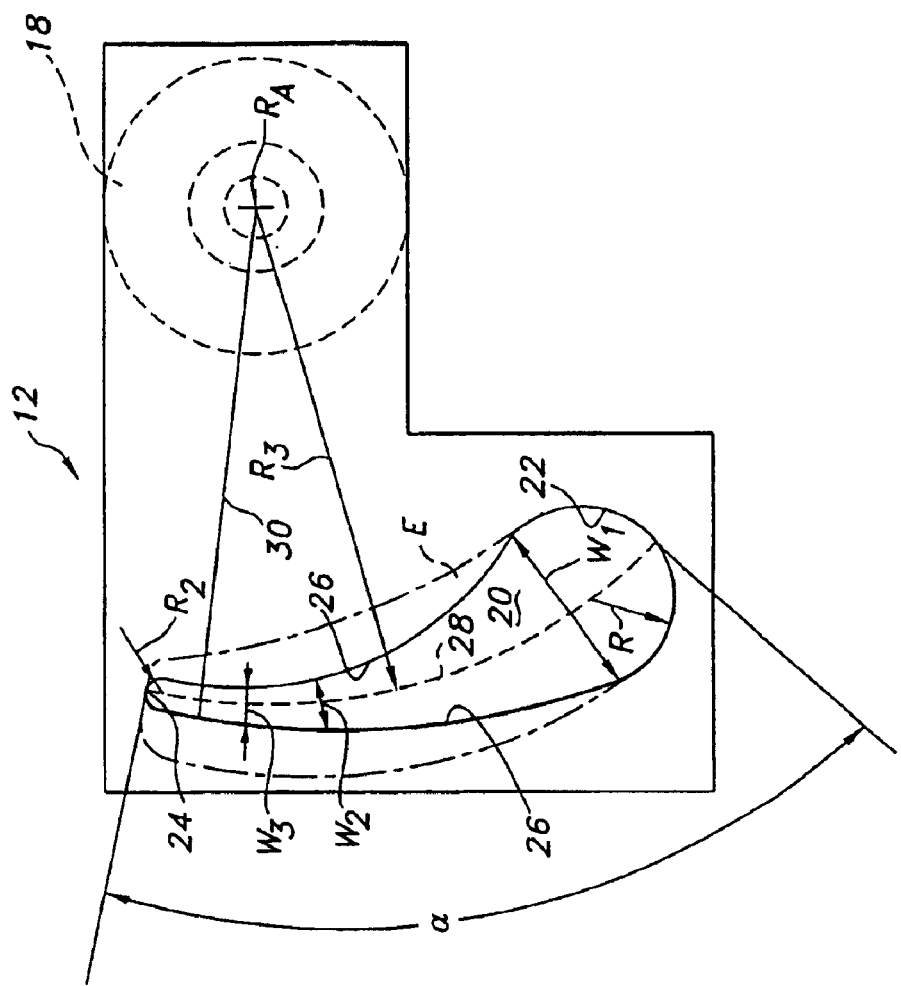
FIG. 3 is a top view of a template of the system.

With reference to FIG. 3, the template 12 is formed with an elongated, continuous channel 20 that extends therethrough. The specific shape of the channel 20 (length; widths) is dictated by the desired intensities of UV energy to be emanated from the system 10. By way of non-limiting example, as shown in FIG. 3, the channel 20 may be formed with a first end 22 which is arcuate and formed about a first radius R, and a second end 24 that is arcuate and formed about a second radius R2. Preferably, the radius R is greater than the radius R2. Side walls 26 of the channel 20 extend between and blend with the first and second ends 22, 24. A central axis 28 extends along the length of the channel 20 which coincides with the centers for the radii R and R2. The central axis 28 may be defined about a single radius R3 which extends from an axis of rotation of the template 12, designated with the reference RA. The channel 20 defines an arc that subtends an angle α of at least 40 degrees (relative to the axis of rotation RA). Preferably, the angle α is approximately 65°. Since the template 12 need not be rectangular, it is preferred that the template 12 be formed with minimal material. For example, as shown in FIG. 3, with the depicted channel 20 shape, the template 20 may be L-shaped.

In addition, the channel 20 may be non-symmetrically formed about any axis that is coplanar with the central axis 28 and intersects the axis of rotation RA. For example, the channel 20 is non-symmetrically formed about reference axis 30 (FIG. 3). Likewise, the channel 20 is non-symmetrically formed about the reference axis 30 if it were to coincide with the radius R3.

The UV lamp 14 may be of any type known to those skilled in the art. It is desired to coincide the central axis 28 with the inlet aperture 108 of the light guide 106 so that the central axis 28 passes therepast during the course of relative movement. It is further desired to continuously align the center of the inlet aperture 108 with the central axis 28 during the course of relative movement.

Furthermore, a shutter (not shown) may be connected to the light guide 106 to selectively control UV energy emanating from the system 10. The opening and closing of the shutter may be controlled by a solenoid 116 and may be synchronized with the relative movement between the template 12 and the UV lamp 14. If so, the course of relative movement between the template 12 and the UV lamp 14 will begin with the opening of the shutter and end with the closing thereof Preferably, the shutter is located to selectively control UV energy entering the inlet aperture 108.

As can be appreciated, due to the shape of the channel 20, different channel widths (e.g., $W_1$, $W_2$, $W_3$ . . . ) are located along the length of the channel 20 which permit different amounts of UV energy to pass therethrough during the course of relative movement. In one possible arrangement, as shown in FIG. 3, the widths $W_1$, $W_2$, $W_3$ are continuously changing along the length of the central axis 28, and continuously diminishing between the first end 22 and the second end 24. Widths $W_1$, $W_2$, $W_3$ are measured in a direction oblique to the axis of rotation RA, and, preferably, are coplanar with and perpendicular to the central axis 28.

The template 12 acts to shield the inlet aperture 108 from varying amounts of focused UV energy E. The template 12 varies the intensity of the UV energy through physical shielding. It should be noted that the intensity of the energy emanating from the UV lamp may also be altered for further control. Although the intensities of UV energy which is emanated vary, the emanation of UV energy is continuous throughout the course of relative movement.

Although not shown, relative movement between the template 12 and the UV lamp 14 can be achieved through a movement of the UV lamp 14 alone, the template 12 alone, and a combination thereof. Also, various forms of motion can be utilized beyond rotational motion, such as straight-line motion. As such, the general shape of the channel 20 is formed accordingly.

As an exemplary embodiment, the motor 18 is controlled by a controller 34 and powered by a driver/indexer board, such as that sold under the tradename DCB-241 I by Advanced Micro Systems, Inc. The controller 34 includes a data storage (e.g., an EPROM) to store motion programs prepared to control output of the motor 18. In addition, the controller 34 synchronizes the opening and closing of the shutter (via connector 17) with the beginning and end, respectively, of the course of relative movement between the template 12 and the UV lamp 14. The controller 34 may also control the UV lamp 14, e.g., via connector 19.

In operation, the UV lamp 14 is activated to emanate a focused UV energy beam E through the light guide 106. The controller 34 causes relative movement between the template 12 and the UV lamp 14 upon the UV energy being emitted. If a shutter is to be used, the relative movement is initiated upon opening of the shutter. In either manner, the focused UV energy E is caused to pass through the channel 20.

To illustrate further operation of the invention, it will be assumed that the focused UV energy E will pass through the first end 22 initially. The channel 20 passes the UV lamp 14 with varying intensities of the focused UV energy E passing therethrough as the channel 20 moves relatively past the UV lamp 14. As shown in phantom lines in FIG. 3, the UV energy will be shielded, to varying extents, by the template 12. (FIG. 3 schematically represents a relatively constant focused UV energy beam E being emitted from the UV lamp 14.) As stated above, it is desired that the center of the inlet aperture 108 be aligned with the central axis 28. In addition, it is desired to align the center of the focused UV energy beam E with the central axis 28. Upon the second end 24 coinciding with the UV energy beam E, the controller 34 acts to stop the emission of UV energy E by deactivating the UV lamp 14 and/or closing the shutter. As a result of this operation, material can be cured continuously with varying intensities of UV energy E.

Other operations are possible. For example, rather than provide a continuously diminishing dosage of UV energy (which will result in the example above with the first end 22 being initially aligned with the UV lamp 14), a continuously increasing dosage may be generated (e.g., with the second end 24 being initially aligned with the UV lamp 14 and relative movement being caused with the first end 22 moving relatively towards the UV lamp 14), or a varying dosage.

Figure 4:
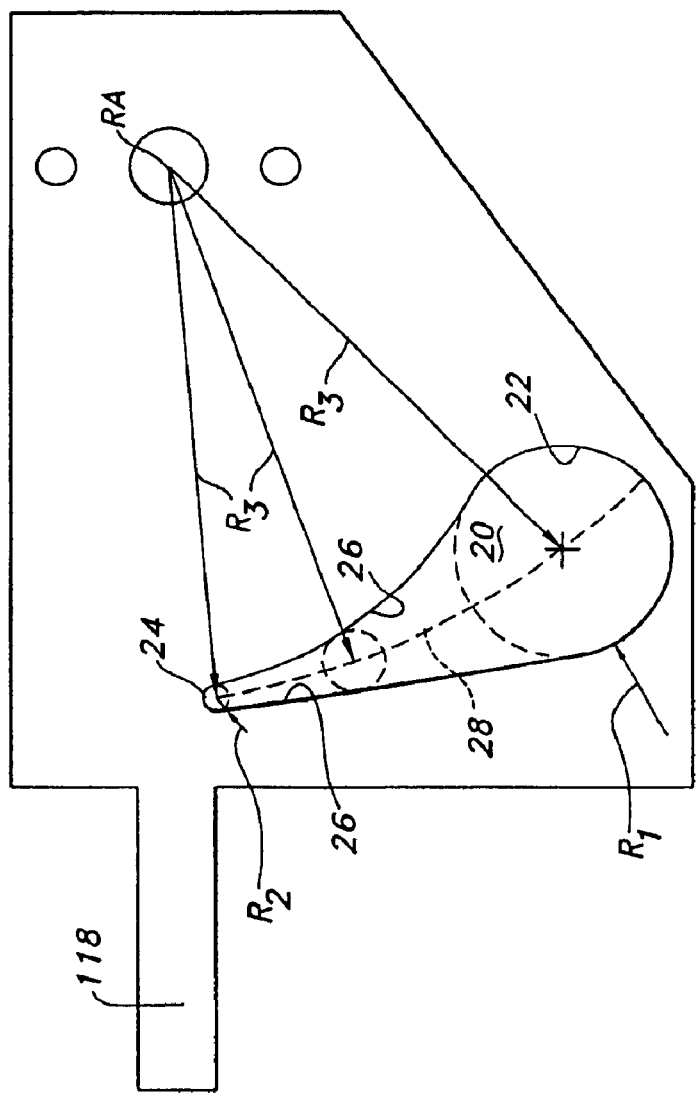
FIG. 4 is a second embodiment of the template having an appendage extending therefrom; and, FIG. 5 is a schematic of an optical positioning system used in connection with the subject invention.
Figure 5:
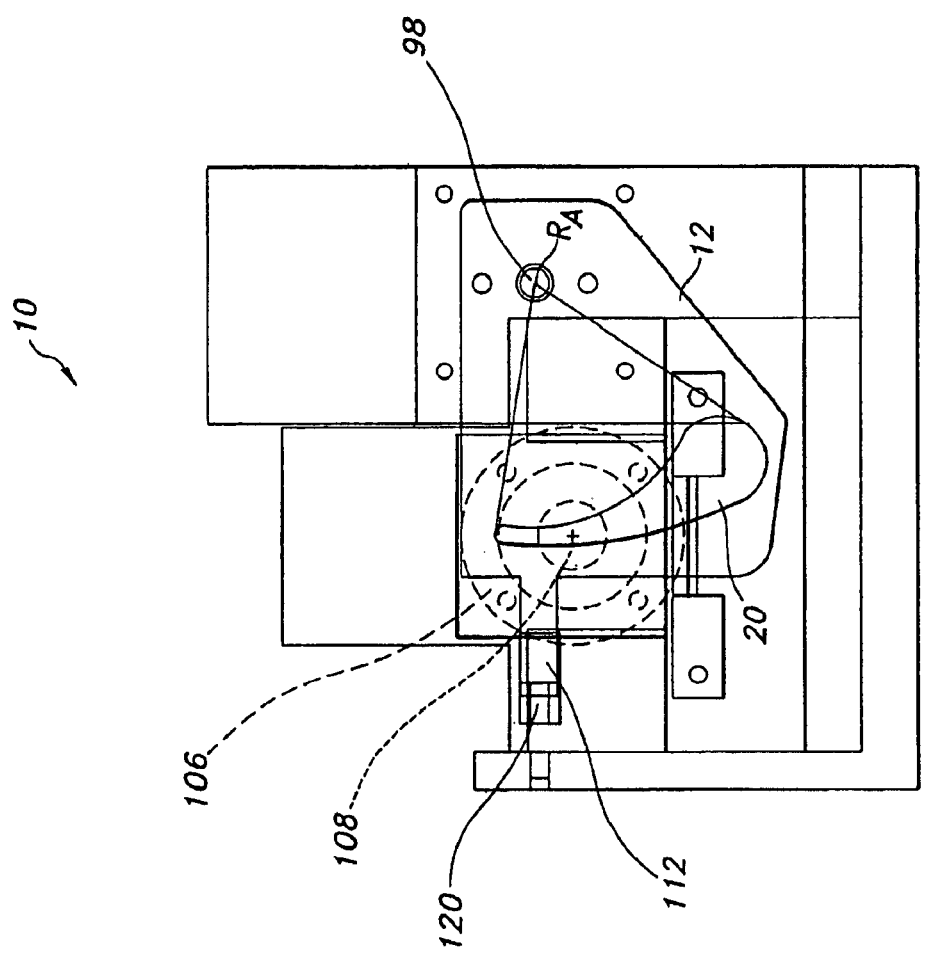

To ensure proper repeated position of the channel 20 relative to the UV lamp 14, an optical positioning system may be provided. With reference to FIG. 4, an appendage 118 protrudes from the template 12. With reference to FIG. 5, an optical position sensor 120 is located such that, upon rotation of the template 12, the appendage 118 is caused to trigger the optical position sensor 120 (e.g., by at least partially crossing a reference beam) with the template 12 reaching a start position. The optical positioning sensor 120 may be connected to the controller 34 and/or the motor 18 to stop further rotation thereof. In addition, an optical limit switch may be provided to connect with the appendage 118 to indicate a finish position of the course of relative movement. The optical limit switch may be connected to the controller 34, the motor 18, the UV lamp 14 (to cause deactivation thereof), and/or a shutter (e.g., via the solenoid connector 116 to cause closing thereof) so as to stop further rotation and prevent further UV energy to be emanated from the system 10. The optical sensor 120 and the optical limit switch may be mounted onto the base plate 112 using brackets 122, 124, respectively (FIG. 2).

As is readily apparent, the system 10 can be used for single-controlled discrete curing applications, or used in a repeated setting, such as on an assembly line. For a repeated setting, with the optical positioning system, the system 10 can be programmed to accurately and repeatedly actuate a fixed operation and be re-set to a start position in administering consistently a radiation exposure cycle. Through the controller 34, features of the radiation exposure cycle may be adjusted, such as intensity of the radiation and exposure time of the radiation (e.g., speed of relative movement between the template 12 and the UV lamp 14 may be adjusted; power level of the UV lamp 14 may be adjusted).

The invention being thus described, it will be clear that the same may be varied in many ways. Such variations are not to be regarded as a departure from the spirit and scope of the invention and all modifications are intended to be included within the scope of the claims.

What is claimed is:

1. An electromagnetic energy spot curing system comprising:
   a source of radiation in the electromagnetic spectrum;
   a template having at least one fixed channel formed therethrough, wherein said channel extends along a central axis, said channel having a plurality of various widths located at various points along said central axis, said widths being disposed transversely to said central axis; and
   a driver for causing relative motion between said template and said source, wherein said channel being positioned and configured to allow differing amounts of radiation emanating from said source to continuously pass through said channel during the course of relative movement between said template and said source.

2. A system as in claim 1, wherein said channel defines an arc that subtends an angle of at least 40 degrees.

3. A system as in claim 1, wherein said channel defines a plurality of widths.

4. A system as in claim 1, wherein said template rotates about an axis of rotation, and said widths being measured in a direction oblique to said axis of rotation.

5. A system as in claim 1, wherein said channel includes spaced-apart first and second ends, said first end being arcuate and defined about a first radius, said second end being arcuate and defined about a second radius, said first radius being greater than said second radius.

6. A system as in claim 5, wherein said channel includes arcuate side walls extending between and blending with said first and second ends.

7. A system as in claim 1, wherein said channel is formed with first and second ends spaced-apart along said central axis, a plurality of reference axes being defined coplanar to said central axis, said reference axes each intersecting both an axis of rotation of said template and said central axis, wherein said channel being non-symmetrically formed about each said reference axis.

8. A system as in claim 1, wherein said source is a UV lamp.

9. A system as in claim 1, wherein said driver is a motor.

10. A method of spot curing a curable material using radiation in the electromagnetic spectrum, said method comprising the steps of:
    providing a template having at least one fixed channel formed therethrough, said channel extending along a central axis, said channel having a plurality of various widths located at various points along said central axis, said widths being disposed transversely to said central axis;
    providing a source of the radiation in the electromagnetic spectrum;
    allowing radiation to emanate from said source;
    aligning a portion of said channel of said template with said source such that at least a portion of said radiation passes therethrough; and
    causing relative motion between said template and said source so that said channel continuously allows differing amounts of radiation to pass through said channel during the course of relative movement.

11. A method as in claim 10, wherein said step of allowing energy to emanate from said source is controlled by selective opening of a shutter.

12. A method as in claim 11, wherein said shutter is maintained open during the course of relative movement.

13. A method as in claim 12, wherein said step of causing relative motion between said template and said source is caused by rotation of said template.

14. An electromagnetic energy spot curing system comprising:
    a means for generating radiation in the electromagnetic spectrum;
    a template having at least one fixed channel formed therethrough, said channel extending along a central axis, said channel having a plurality of various widths located at various points along said central axis, said widths being disposed transversely to said central axis; and
    means for causing relative motion between said template and said generating means, wherein said channel is positioned and configured to allow differing amounts of radiation emanating from said generating means to continuously pass through said channel during the course of relative movement between said template and said generating means.

15. A system as in claim 14, wherein said generating means is a UV lamp.

16. A system as in claim 14, wherein said relative motion means is a motor.

17. An electromagnetic energy spot curing system comprising:
    a source of radiation in the electromagnetic spectrum;
    a template having at least one channel formed therethrough; and
    a driver for causing relative motion between said template and said source, wherein said channel is positioned and configured to allow differing amounts of radiation emanating from said source to continuously pass through said channel during the course of relative movement between said template and said source, wherein said channel is elongated and defines an arc that subtends an angle of at least 40 degrees, and wherein said template rotates about an axis of rotation, said channel having a central axis defined about a single radius extending from said axis of rotation.

18. A system as in claim 17, wherein said widths are measured in a direction oblique to said axis of rotation.

19. A system as in claim 17, wherein said channel is formed with first and second ends spaced-apart along a central axis, said widths being measured perpendicularly to said central axis.

20. An electromagnetic energy spot curing system comprising:
  a source of radiation in the electromagnetic spectrum;
  a template having at least one channel formed therethrough; and
  a driver for causing relative motion between said template and said source, wherein said channel is positioned and configured to allow differing amounts of radiation emanating from said source to continuously pass through said channel during the course of relative movement between said template and said source, wherein said channel defines a plurality of widths and wherein said template rotates about an axis of rotation, and said widths are measured in a direction oblique to said axis of rotation.

21. A system as in claim 20, wherein said channel is elongated.

22. A system as in claim 20, wherein said channel has a central axis defined about a single radius extending from said axis of rotation.

23. A system as in claim 20, wherein said channel is formed with first and second ends spaced-apart along a central axis.

24. An electromagnetic energy spot curing system comprising:
  a source of radiation in the electromagnetic spectrum;
  a template having at least one channel formed therethrough; and
  a driver for causing relative motion between said template and said source, wherein said channel is positioned and configured to allow differing amounts of radiation emanating from said source to continuously pass through said channel during the course of relative movement between said template and said source, wherein said channel includes spaced-apart first and second ends, said first end being arcuate and defined about a first radius, said second end being arcuate and defined about a second radius, said first radius being greater than said second radius.

25. A system as in claim 24, wherein said channel is elongated.

26. A system as in claim 24, wherein said template rotates about an axis of rotation, said channel having a central axis defined about a single radius extending from said axis of rotation.

27. A system as in claim 24, wherein said template rotates about an axis of rotation, said widths being measured in a direction oblique to said axis of rotation.

28. An electromagnetic energy spot curing system comprising:
  a source of radiation in the electromagnetic spectrum;
  a template having at least one channel formed therethrough; and
  a driver for causing relative motion between said template and said source, wherein said channel is positioned and configured to allow differing amounts of radiation emanating from said source to continuously pass through said channel during the course of relative movement between said template and said source, wherein said channel is formed with first and second ends spaced-apart along a central axis, a plurality of reference axes being defined coplanar to said central axis, said reference axes each intersecting both an axis of rotation of said template and said central axis, wherein said channel being non-symmetrically formed about each said reference axis.

29. A system as in claim 28, wherein said channel is elongated.

30. A system as in claim 28, wherein said template rotates about an axis of rotation, said channel having a central axis defined about a single radius extending from said axis of rotation.

31. A system as in claim 28, wherein said template rotates about an axis of rotation, said widths being measured in a direction oblique to said axis of rotation.

32. A method of spot curing a curable material using radiation in the electromagnetic spectrum, said method comprising the steps of:
  providing a template having at least one channel formed therethrough;
  providing a source of the radiation in the electromagnetic spectrum;
  allowing radiation to emanate from said source;
  aligning a portion of said channel of said template with said source such that at least a portion of said radiation passes therethrough; and
  causing relative motion between said template and said source so that said channel continuously allows differing amounts of radiation to pass through said channel during the course of relative movement, wherein said step of allowing energy to emanate from said source is controlled by selective opening of a shutter.

* * * * *